United States Patent [19]
Geiss et al.

[11] Patent Number: 4,834,724
[45] Date of Patent: May 30, 1989

[54] DEVICE FOR ASPIRATING FLUIDS FROM A BODY CAVITY OR HOLLOW ORGAN

[76] Inventors: Alan C. Geiss, 50 Prampton Ln., Grect Neck, N.Y. 11023; Eugene L. Flanagan, 23 Bayview Ter., Manhasset, N.Y. 11030

[21] Appl. No.: 34,749

[22] Filed: Apr. 6, 1987

[51] Int. Cl.$^4$ .............................................. A61M 25/00
[52] U.S. Cl. .................................... 604/280; 604/104; 604/268; 433/96
[58] Field of Search ........................ 604/27, 28, 54, 93, 604/96–103, 104, 107, 264, 266, 268, 281, 284, 105; 128/304; 433/91, 93, 95

[56] References Cited

U.S. PATENT DOCUMENTS

| | | | |
|---|---|---|---|
| 2,106,433 | 1/1938 | Morse | 604/41 |
| 2,756,752 | 7/1956 | Scherlig | 128/303 R |
| 3,860,006 | 1/1975 | Patel | 604/281 |
| 3,999,554 | 12/1976 | Kim et al. | 604/268 |
| 4,030,503 | 6/1977 | Clark, III | 128/304 |
| 4,158,916 | 6/1979 | Adler | 604/268 |
| 4,217,904 | 8/1980 | Zahorsky | 604/268 |
| 4,531,933 | 7/1985 | Norton et al. | 604/281 |
| 4,681,564 | 7/1987 | Landreneau | 604/96 |
| 4,681,570 | 7/1987 | Dalton | 604/282 |

FOREIGN PATENT DOCUMENTS 1249957  10/1971  United Kingdom ................ 604/281

*Primary Examiner*—Dalton L. Truluck

[57] ABSTRACT

A device for aspirating fluids from a body cavity or hollow organ. The device includes an elongated tube having a proximal opening adapted to be coupled to a suctioning device. The elongated tube also has a portion spaced from the proximal opening to be positioned in the cavity or organ. The portion is convolved about a central axis and has at least one aspirating port facing inwardly of the convolved portion for spacing the at least one aspirating port from the walls of the cavity or organ.

15 Claims, 2 Drawing Sheets

DEVICE FOR ASPIRATING FLUIDS FROM A BODY CAVITY OR HOLLOW ORGAN

BACKGROUND OF THE INVENTION

The present invention relates to suction tubes for removing fluids from the gastrointestinal tract. More particularly, the present invention concerns novel tubes so arranged as to avoid sucking up the linings of the stomach and the complications which arise therefrom.

In patient care, it is frequently necessary to remove secretions from within the gastrointestinal tract on a continuing basis. Following intestinal surgery, for example, normal gastrointestinal function is temporarily impaired and the stomach then tends to fill up with gastric secretions and air. The patient consequently becomes distended and nausea and vomiting will ensue. This distention and vomiting can disrupt healing anastamoses and prolong the gastric ileus. Patients suffering from intestinal obstruction likewise will experience vomiting in the natural effort to rid the stomach of accumulated liquids and air. In these patients it is essential to aspirate out the secretions and swallowed air to prevent further distention of the intestines and avoid the complications of spontaneous perforation or gangrene of the intestines. This aspiration is also a mainstay of initial therapy in patients with intestinal obstruction.

The use of suction tubes to evacuate fluids from within the body, for these and other purposes has long been known in the prior art. The so-called "Levin tube", which is even today the most widely used gastric suction tube, was described by A. L. Levin in 1921. "New Gastroduodenal Catheter", *Journal of the American Medical Association*, Volume 76, p. 1007, 1921. The Levin tube is a long, flexible, single-lumen tube adapted to be introduced into the stomach through the nasal passages and the esophagus. A number of ports for communicating gastric fluids to the interior of the tube are arranged longitudinally adjacent the distal end of the tube. Upon the application of suction to the proximal end of the tube, therefore, stomach fluids are removed through the ports and the interior of the tube to a collection vessel.

The stomach lining or mucosa sits loosely in folds throughout the interior of the stomach and is easily separated from the underlying layers. The medical profession has long recognized that the ports of the single-lumen tube are liable to be blocked by the mucosa when suction is being applied to the tube. See for example, G. Cleland, "A Gastric Aspiration-Tube", *The Lancet*, Oct. 29, 1955, pp. 908–909; R. K. Hughes et al., "Gastric sump drainage with a water seal monitor", *Surgery*, Volume 61, No. 2, February, 1967, pp. 192–195; and E. F. Schmerl et al., "Porthole Ulcers Associated with Gastric Intubation", *The Western Journal of Medicine*, Volume 124, February, 1976, pp. 172–173. These authors all report a causal link between tube blockage by the gastric mucosa and the development of traumatic ulcers during such intubation. The consequences may be limited to pain and discomfort, but patients can also suffer serious blood loss from mucosal ulcerations.

Accordingly, the medical profession has long felt the need to provide a suction tube which avoids the foregoing disadvantages of the single-lumen tube. One proposed solution is to provide a double-lumen tube wherein a partial vacuum is applied to one lumen to remove gastric fluids. A second lumen or sump opens into the first lumen permitting a flow of air into the first lumen adjacent the distal end. It is intended that by introducing this flow of air into the first lumen, the vacuum created when the mucosa is sucked into its ports will be broken.

However, it has been reported that ulceration of the mucosa occurs, nevertheless, following intubation with a double-lumen tube. J. F. Greene, Jr., et al., "Gastric Ulceration: A Complication of Double-Lumen Nasogastric Tubes", *Journal of the American Medical Association*, Volume 224, No. 3, April 16, 1973, pp. 338–339. Greene et al. report four cases in which autopsies revealed superficial gastric ulcers spacially arranged identically to the sucking ports of the double-lumen nasogastric tube, and concluded that this ulceration was caused by sucking the mucosa into the lumen.

SUMMARY

One general object of this invention, therefore, is provide a new and improved device for aspirating fluids from a body cavity or hollow organ without causing inflammation and ulceration of its lining.

More specifically, it is an object of the invention to provide such a device wherein the aspirating ports are prevented from contacting the lining of the body cavity or hollow organ whereby they are prevented from sucking it in.

Another object of the invention is to provide such a device having improved patency in use.

A further object of the invention is to provide such a device which is easily inserted into the body cavity or hollow organ and removed therefrom when no longer required.

In one illustrative embodiment of the invention, a nasogastric tube is provided having a proximal opening adapted to be coupled to a suctioning device. The tube also has a portion spaced from the proximal opening to be positioned in the stomach. The portion is formed in an elongated helix and has one or more aspirating ports facing inwardly of the helical portion for spacing such ports from the gastric mucosa. Accordingly, the aspirating ports face toward the central axis and away from the body's tissue. Fluids within the stomach are nevertheless permitted to flow between the helical turns of the tubing to be sucked up by the aspirating ports upon application of a negative pressure to the proximal end of the tube.

In accordance with one feature of the invention, a support shaft is positioned within the helical portion of the nasogastric tube. The inner surface of the helical portion is affixed thereto thus to maintain its shape, as well as to lend axial rigidity thereto for insertion into the stomach. Preferably, the support shaft is also affixed to axially disposed portions of the nasogastric tube joined to the ends of the helical portion for improved axial rigidity.

In accordance with another feature of several advantageous embodiments of the invention, a plurality of spacers join adjacent turns of the helical portion of the nasogastric tube to maintain the turns in predetermined spaced relation.

In accordance with another feature of the invention, in certain important embodiments, the helical portion of the nasogastric tube is made of flexible material and the nasogastric tube further comprises means for straightening the helical portion for insertion into the stomach.

In accordance with yet another feature of the invention, a method and device are provided for aspirating fluids from a body cavity or hollow organ. The device includes an elongated tube having a distal portion being formed in an elongated helix having one or more aspirating ports. All of the aspirating ports face inwardly of the helical portion.

In accordance with said method, the distal portion of the tube is positioned in the body cavity or hollow organ. A suctioning device is coupled to a proximal portion of the tube and suction is applied thereto. Since the aspirating ports face inwardly of the helical portion, the ports are spaced from the walls of the cavity or organ.

BRIEF DESCRIPTION OF THE DRAWINGS

The present invention, as well as further objects and features thereof, will be understood more clearly and fully from the following description of certain preferred embodiments, when read with reference to the accompanying drawings, in which.

DESCRIPTION OF CERTAIN PREFERRED EMBODIMENTS

Figure 1:
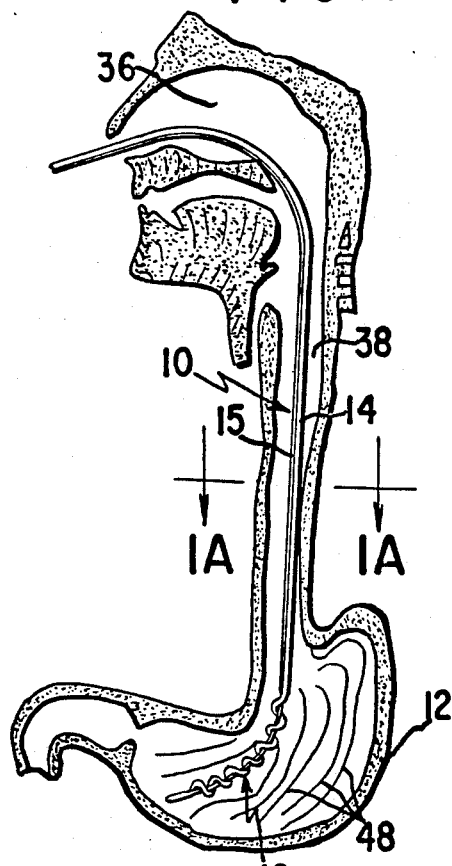
FIG. 1 is a cross-sectional view of a portion of the human body extending from the nasopharynx to the duodenum, illustrating a nasogastric tube in accordance with one illustrative embodiment of the present invention in place for aspirating fluids from the stomach.
Figure 1A:
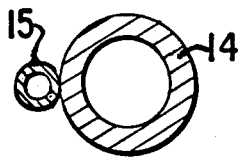
FIG. 1A is a cross-sectional view of the embodiment of FIG. 1, taken along the lines 1A—1A thereof.
Figure 2A:
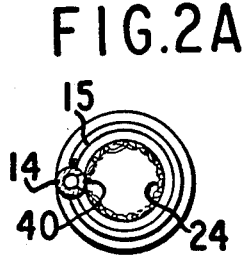
FIG. 2A is a cross-sectional view of the embodiment of FIG. 2, taken along the lines 2A—2A of FIG. 2.

With reference first to FIG. 1, a nasogastric tube 10 in accordance with one embodiment of the present invention is shown positioned in a patient's stomach 12 for aspirating fluids therefrom. Tube 10 includes a first elongated lumen 14 through which stomach fluids are aspirated by suction. Tube 10 also includes a second elongated lumen 15 parallel with and affixed to the first lumen 14 to act as a sump for the first lumen in a conventional manner.

Figure 2:
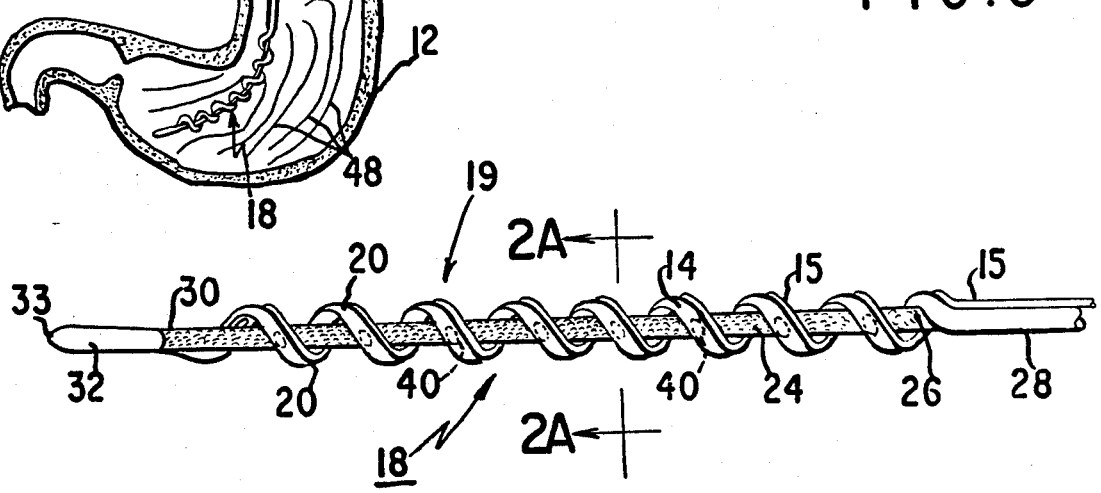
FIG. 2 is a diagrammatic view of the distal end of the nasogastric tube embodiment shown in FIG. 1, taken transverse to the longitudinal axis thereof.

Tube 10 as shown in FIG. 1 has a distal section 18 lying within the stomach 12. With reference to FIG. 2, a portion 19 of distal section 18 is formed in a helix having a plurality of turns 20 convolved about and affixed to an axially disposed support shaft 24. In the embodiment of FIG. 2, support shaft 24 is a foraminous, hollow cylinder fabricated from a net of woven fibers. Suitable materials for support shaft 24 include a woven mesh made of polyethylene fiber sold under the trademark Marlex. The turns 20 of portion 19 preferably are spaced about three millimeters apart on support shaft 24.

Support shaft 24 has a proximal end 26 affixed to an axially disposed proximal end 28 of tube 10 and a distal end 30 affixed to an axially disposed distal end 32 of tube 10. Distal end 32 is approximately 4 cm. long and has a closed tapered end 33. Distal end 32 serves as a leader for inserting nasogastric tube 10 through the patient's nasopharynx 36 and esophagus 38 in the stomach 12. Accordingly, axial resistance encountered by distal end 32 is transmitted through support shaft 24 to the proximal end 28 of tube 10. Support shaft 24 in combination with the helical portion 19 of tube 10 is preferably selected to have an axial rigidity approximately equal to that of ends 28 and 32 of tube 10 to facilitate the insertion of tube 10 as described above.

Support shaft 24 is affixed by heating or with a suitable adhesive to the surface of lumen 14 facing inwardly of the helical portion 19. A plurality of aspiration ports 40 for communicating gastric fluids to lumen 14 are formed in the inner surface therethrough and preferably through support shaft 24. Since support shaft 24 extends continuously within the helical distal portion adjacent the inner wall, it serves as a means to isolate body tissues (such as the mucosa) from the aspiration ports. By affixing the support shaft 24 to either the helical portion or to the ends 28 and 30, or else to all of the above, a means is provided for maintaining the tube in elongated helical configuration.

Figure 3:
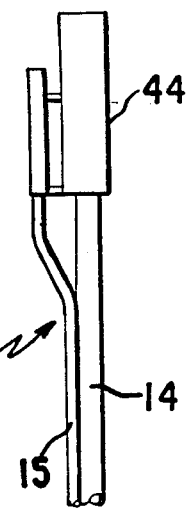
FIG. 3 is a diagrammatic view of the proximal end of the nasogastric tube embodiment shown in FIG. 1 showing a device for coupling one lumen thereof to a suctioning device.

With reference to FIG. 3, the proximal end of tube 10 has a cylindrical coupling 44 affixed thereto for applying a suction to lumen 14. Referring to FIGS. 1 and 2, the application of suction to lumen 14 causes stomach fluids, such as gases and gastric secretions, to be drawn through the foraminous support shaft 24 and then into lumen 14 through ports 40. These fluids exit the lumen 14 through coupling 44 and are gathered in collection vessel.

As stated above, the use of prior art nasogastric tubes for suctioning gastric fluids can lead to the ulceration of the stomach lining or mucosa with potentially serious consequences. The shape, size and spacing of the ulcers observed evidence that the cause of such ulceration is the clogging of the aspiration ports with the gastric mucosa due to the negative pressure in the tube. As shown generally in FIG. 1, the gastric mucosa forms longitudinal rows indicated at 48 and known as the magenstrassa. Accordingly, the placement of a prior art nasogastric tube into the stomach tends to align it lengthwise with the magenstrassa. As is well known, the stomach mucosa is thick, very flexible and relatively easily separated from the underlying layers of the stomach. Therefore, the prior art nasogastric tube aligned with the magenstrassa tends to become enveloped by the mucosa thus clogging the outwardly facing aspirating ports. Consequently, the mucosa tends to be drawn into the tube, thereby causing the mucosa to distend and become irritated.

As explained above, the embodiment of the present invention shown in FIG. 2 provides a portion 19 of the tube 10 formed in a helix with a plurality of aspiration ports 40 facing inwardly thereof. Ports 40, therefore, face away from the gastric mucosa and are physically spaced therefrom by the tube itself. As suction is applied to the lumen 14, fluids accessible to the interior of the helix will be drawn from the stomach. Since the portion 19 is formed in a helix, however, a helical space exists between turns 20 thereof, thus distributing the suction from ports 20 both radially and axially to decrease the effect of the suction on the mucosa. Moreover, the disposition of the turns 20 at an angle to the magenstrassa 48 decreases the tendency of the mucosa to envelope the tube. Finally, in the embodiment of FIG. 2, the use of the foraminous shaft 24 within the helix prevents the aspirating ports 40 from being clogged by larger particles.

Figure 4:
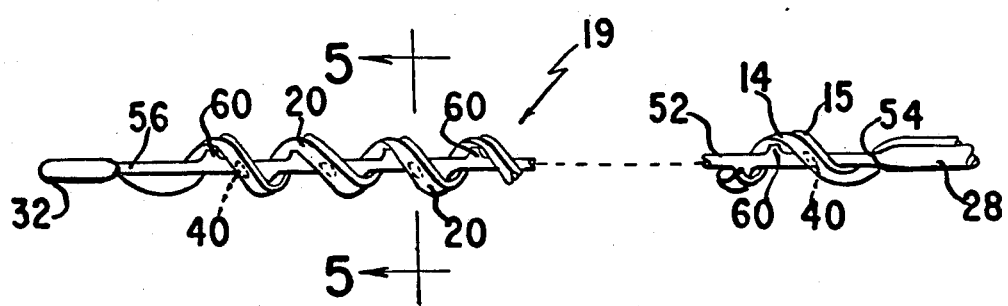
FIG. 4 is a diagrammatic view of a portion of the distal end of a nasogastric tube in accordance with a further illustrative embodiment of the present invention, taken transverse to the longitudinal axis thereof.
Figure 5:
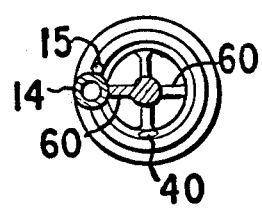
FIG. 5 is a cross-sectional view of the embodiment of FIG. 4 taken along the lines 5—5 thereof.

FIGS. 4 and 5 illustrate a further embodiment of the present invention. Elements shown in FIGS. 4 and 5 corresponding to those shown in FIGS. 1 and 2 are indicated by the same reference numerals. A rod 52 is disposed centrally of the helical portion 19 and is affixed at its proximal end 54 to proximal end 28 of tube 10 and at its distal end 56 to distal end 32 of tube 10 to provide axial rigidity to portion 19. Rod 52 is made of a material which is sufficiently flexible to permit the introduction of tube 10 through the nasopharynx 36 and esophagus 38 into stomach 12, as well as to permit portion 19 to bend within stomach 12.

Rod 52 also has a plurality of spokes 60 radiating therefrom and spaced axially therealong for affixing to lumen 14. Accordingly, rod 52 and spokes 60 maintain the spacing of turns 20 of portion 19.

Figure 6:
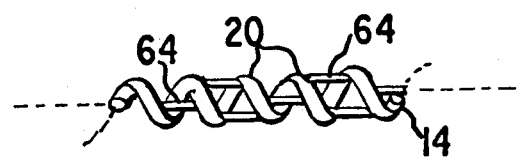
FIG. 6 is a partial diagrammatic view of still another illustrative embodiment of the present invention, taken transverse to the longitudinal axis thereof.

In the further embodiment of FIG. 6, wherein corresponding elements are indicated by the same reference numerals, a plurality of spacers 64 join adjacent turns 20 of lumen 14 to maintain them in predetermined spaced relation. The axial forces on lumen 14 are transmitted through spacers 64, which thus provide axial rigidity. Spacers 62 are preferably made of a material capable of compression and extension to permit the helical portion to bend sufficiently for introduction into the stomach and movement therein. A sump tube may be disposed inwardly of the helix, if desired.

Figure 7A:
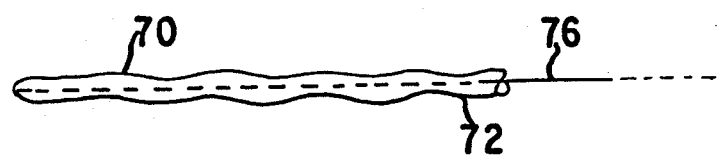
FIGS. 7A and 7B show one illustrative means for straightening the distal portion of a nasogastric tube in accordance with the present invention for introducing the tube into the stomach.
Figure 7B:
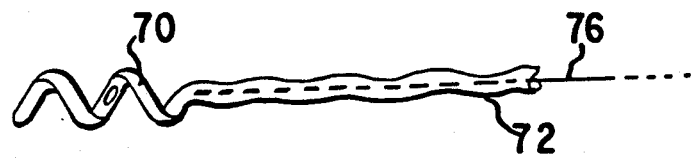
Figure 8:
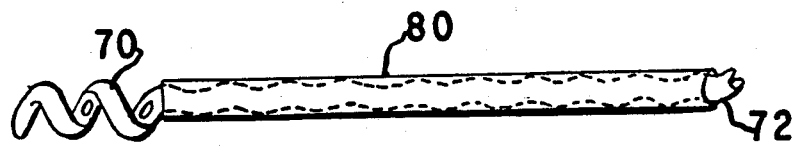
FIG. 8 shows still another means for introducing a nasogastric tube in accordance with the present invention into the stomach.

FIGS. 7A, 7B and 8 illustrate a method of introducing a convolved aspiration tube of flexible material into a hollow organ or body cavity. In FIG. 7A, the distal end 70 of an aspiration tube 72 is straightened for introduction into the body by a stent 76 slidably disposed therein. Stent 76 is relatively more rigid than distal end 70 for straightening it, but sufficiently flexible to permit introduction of tube 72 with stent 76 therein into the body. After tube 72 is in place, stent 76 is withdrawn therefrom sufficiently to permit distal end 70 to assume its pre-formed shape, in this embodiment a helix, as shown in FIG. 7B.

FIG. 8 illustrates an alternative straightening means for introducing tube 72 into a body cavity or hollow organ. A sleeve 80 is slidably mounted initially over the exterior of the distal end 70 of tube 72 for straightening it. Sleeve 80, like stent 76, is made of a relatively flexible material to permit it to bend sufficiently for introduction into the body. As shown in FIG. 8, after introduction of tube 72, sleeve 80 is withdrawn sufficiently to permit the distal end 70 of tube 72 to assume its pre-formed shape.

In accordance with a method of making the nasogastric tube embodiments of FIGS. 1–6, a double-lumen tube made, for example, of polyethylene is provided. A flexible rod is inserted into one end each of the two lumens, in order to maintain their patency during the formation of the helix. Then this end of the tube is wound helically about a cylindrical support and is heat formed into a helical shape. The aspirating ports may be heat formed or punched before, during or after the heat forming step creating the helix. After the tube has cooled, the rods are removed therefrom and the distal end is heat sealed. In the case of the embodiment of FIG. 2, the tube is wound about the cylindrical support shaft 24 and affixed thereto by heat, adhesive or other suitable means. In the case of the embodiments of FIGS. 4–6, the rod 52 and the spacers 64 can be made, for example, of polyethylene and affixed to the lumen 14 by heating.

An intermediate portion of tube 10 may be constructed in accordance with the teachings of U.S. Pat. No. 4,363,323 in the name of Alan C. Geiss entitled "Nasogastric Tube Adapted to Avoid Pressure Necrosis" and issued Dec. 14, 1982.

Although the illustrated embodiments of the invention are particularly advantageous for use in aspirating fluids from the stomach, it will be appreciated that the present invention is useful for aspirating fluids from other hollow organs and body cavities. It will also be apparent from a perusal of the present disclosure that various additional configurations for the aspirating device of the present invention are possible.

The terms and expressions which have been employed are used as terms of description and not of limitation, and there is no intention in the use of such terms and expressions of excluding any equivalents of the features shown and described or portions thereof, it being recognized that various modifications are possible within the scope of the invention claimed.

What is claimed is:

1. A nasogastric tube, comprising:
   an elongated tube having a proximal opening adapted to be coupled to a suctioning device;
   the elongated tube further having a distal portion spaced axially from the proximal opening and adapted to be positioned in the stomach;
   the distal portion of the elongated tube being formed in an elongated helix having one or more aspirating ports, all of said aspirating ports facing inwardly of the helical portion for spacing such ports from the gastric mucosa.

2. The nasogastric tube of claim 1, further comprising a support shaft positioned within the helical portion and to which the helical portion is affixed.

3. The nasogastric tube of claim 2, wherein the support shaft comprises a foraminous cylinder.

4. The nasogastric tube of claim 3, wherein the foraminous cylinder comprises a net of woven fibers.

5. The nasogastric tube of claim 2, wherein the support shaft is a central rod having a plurality of spokes spaced axially along and radiating from the rod and affixed to the helical portion.

6. The nasogastric tube of claim 2, wherein the elongated tube comprises a distal end and a proximal end, the helical portion being disposed between the distal and proximal ends and the support shaft being affixed at respective ends thereof to the distal and proximal ends.

7. The nasogastric tube of claim 1, further comprising a plurality of spacers joining adjacent turns of the helical portion to maintain the turns in predetermined spaced relation.

8. The nasogastric tube of claim 1, wherein the helical portion is made of flexible material and the nasogastric tube further comprises means for straightening the helical portion for insertion into the stomach.

9. The nasogastric tube of claim 8, wherein the straightening means comprises a stent slidably mounted within the elongated tube.

10. The nasogastric tube of claim 8, wherein the straightening means comprises a sleeve slidably mounted over the exterior of the elongated tube.

11. A device for aspirating fluids from a body cavity or hollow organ, comprising:
- an elongated tube having a proximal opening adapted to be coupled to a suctioning device;
- the elongated tube having a portion spaced from the proximal opening to be positioned in the cavity or organ;
- the portion being formed in an elongated helix having one or more aspirating ports, all of said aspirating ports facing inwardly of the helical portion for spacing such ports from the walls of the cavity or organ.

12. A method of aspirating fluid from a body cavity or hollow organ, comprising:
- positioning a distal portion of an elongated tube in said body cavity or hollow organ, the distal portion being formed in an elongated helix having one or more aspirating ports facing inwardly of the helical portion for spacing such ports from the walls of the cavity or organ; the helically formed distal portion having an outwardly facing surface lacking aspirating ports such that body tissue coming in contact with said outwardly facing surface is not subjected to suction applied to the interior of the elongated tube;
- coupling a suctioning device to a proximal end of the elongated tube; and
- applying suction to the proximal end of the elongated tube.

13. The method of claim 12, wherein the step of positioning the distal portion comprises positioning the distal portion in the stomach.

14. The method of claim 12, further comprising the step of introducing the distal portion into the cavity or organ while the distal portion is maintained in a reduced cross sectional configuration; and
- wherein the step of positioning the distal portion in the cavity or organ comprises reconfiguring the distal portion in an elongated helix.

15. A device for aspirating fluids from a body cavity or hollow organ, comprising:
- an elongated tube having a proximal opening adapted to be coupled to a suctioning device;
- the elongated tube having a portion spaced from the proximal opening to be positioned in the cavity or organ, the portion being formed in an elongated helix having one or more aspirating ports facing inwardly of the helical portion;
- the elongated helix having an outwardly facing surface lacking aspirating ports such that body tissue coming in contact with said outwardly facing surface is not subjected to suction applied to the interior of the elongated tube.

* * * * *